June 16, 1959 C. MALLERIN Plant Pat. 1,847
ROSE PLANT
Filed Sept. 10, 1958
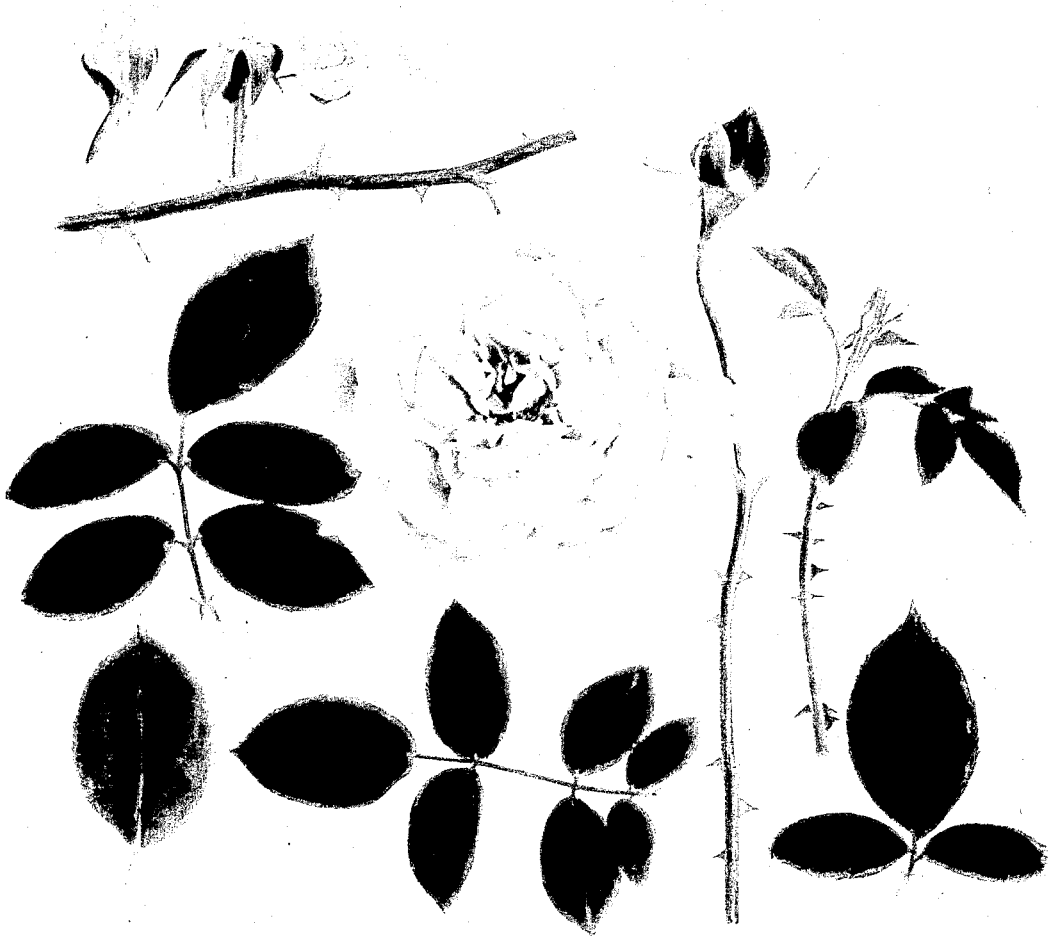
Inventor.
Charles Mallerin
By: Robb & Robb
Attorneys.

United States Patent Office

Plant Pat. 1,847
Patented June 16, 1959

1,847

ROSE PLANT

Charles Mallerin, Varces-Allieres et Risset, France, assignor to The Conard-Pyle Company, West Grove, Pa., a corporation of Pennsylvania Application September 10, 1958, Serial No. 760,281

Claims priority, application France October 7, 1957

1 Claim. (Cl. 47—61)

The present invention relates to a new and distinct variety of rose plant of the hybrid tea class, which was originated by me by crossing an unnamed and unpatented seedling of "Peace" (U.S. Plant Patent No. 591) × "Sondermeldung" (unpatented) with the variety "Grey Pearl" (U.S. Plant Patent No. 680).

The primary objective of this breeding was to produce a new rose variety in which there is combined the vigor and excellent bloom form of the unnamed seedling parent, and the unusual color tones of the blooms of the parent "Grey Pearl." This objective was fully achieved, along with other improvements, as evidenced by the following unique combination of characteristics which are predominant in the new variety and which distinguish it from its parents as well as from all other varieties of which I am aware:

(1) A well-balanced, vigorous habit of growth;

(2) Dark green foliage of medium size;

(3) Excellently formed blooms which are considerably larger and have greater petalage than those of any other variety in the lilac, orchid or lavender color range heretofore known to me; and (4) A pure Pastel Lilac general color tonality of the blooms which is unique in the hybrid tea class and which is retained throughout the life of the blooms without fading.

Asexual reproduction of my new variety by budding, as performed by me in France, and as performed on my behalf at West Grove, Pennsylvania, U.S.A., shows that the foregoing characteristics and distinctions some true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of the new variety, with color terminology in accordance with the Horticultural Color Chart of the Royal Horticultural Society, except where general color terms of ordinary dictionary significance are obvious:

Type: Hardy; bush; outdoor; seedling; for cut flowers and for garden decoration.

Class: Hybrid tea.

Breeding: Seedling.

*Seed parent.*—"Grey Pearl."

*Pollen parent.*—An unnamed seedling of "Peace" × "Sondermeldung."

Propagation: Holds its distinguishing characteristics through succeeding propagations by budding.

*Flower*

Locality where grown and observed: West Grove, Pennsylvania, U.S.A.

Flowers borne: Usually singly, but occasionally several to stem; on strong, long stems.

Quantity of bloom: Free, outdoors.

Continuity: Continuous.

Fragrance: Slight. Nature—tea.

Bud:

*Peduncle.*—Medium length; medium caliper; erect; stiff; rough; with medium number of brown hairs. Color—green, with reddish overcast where exposed to sun.

*Before calyx breaks.*—Size—medium. Form—medium length; pointed; ovoid; with a conspicuous neck; with foliaceous appendages on the surface of the bud; with slender, entire foliaceous parts extending beyond the tip of the bud less than ¼ of its length.

*As calyx breaks.*—Color—Indian Lake, Plate 826/1.

*As first petal opens.*—Size—medium. Form—pointed; ovoid. Color: outside—Indian Lake, Plate 826/1 at outer margin and extending partway down the mid-rib; remainder of petal is an even China Rose, Plate 024, with point of attachment Sulphur Yellow, Plate 1/2; inside—Erythrite Red, Plate 0027/1, with point of attachment Sulphur Yellow, Plate 1/2.

*Opening.*—Opens up well.

Bloom:

*Size (when fully open).*—Medium large; from 5 inches to 6 inches.

*Petalage.*—Double; from 50 to 65 petals; arranged regularly.

*Form.*—High-centered at first, but becoming cupped; petals being at first loosely rolled outward, and remaining loosely rolled outward at maturity.

Petals: Medium thickness; with inside satiny and outside shiny.

*Shape.*—Outer petals—obovate, with one notch. Intermediate petals—obovate, with one notch. Inner petals—round, with one or two notches.

This description of a newly-opened flower was made from a rose grown outdoors in the month of June at West Grove, Pennsylvania, U.S.A.:

*Color.*—Outer petal: outside surface—Amaranth Rose, Plate 530/1 at outer margin, grading to Amaranth Rose, Plate 530/3 and then to Amaranth Rose, Plate 530/1 at base, with point of attachment Primrose Yellow, Plate 601/2; inside surface—Pastel Lilac, Plate 437, lightly veined with Amaranth Rose, Plate 530/1, with point of attachment Primrose Yellow, Plate 601. Intermediate petal: outside surface—Amaranth Rose, Plate 530/3, grading to Amaranth Rose, Plate 530/1 towards base of petal, with point of attachment Primrose Yellow, Plate 601/2; inside surface—Pastel Lilac, Plate 437, lightly veined with Amaranth Rose, Plate 530/1, with point of attachment Primrose Yellow, Plate 601. Inner petal: outside surface—Amaranth Rose, Plate 530/1, with irregular streaks and blotches of Chartreuse Green, Plate 663/3 extending from apex to petal towards the base and merging into Primrose Yellow, Plate 601/2; inside surface—Pastel Mauve, Plate 433, sometimes with a streak of Pod Green, Plate 061/2, and with point of attachment Primrose Yellow, Plate 601.

This description was made from a rose that was open for 3 days outdoors in the month of June at West Grove, Pennsylvania, U.S.A.:

*Color.*—Outer petal: outside surface—Amaranth Rose, Plate 530/2 at outer margin, grading to Amaranth Rose, Plate 530/3 over main area and speckled with Amaranth Rose, Plate 530/1 near base, with point of attachment Primrose Yellow, Plate 601/2; inside surface—near, but slightly darker than, Pastel Lilac, Plate 437 over upper half of petal, grading to Pastel Mauve, Plate 433, with point of attachment Primrose Yellow, Plate 601. Inner petal: outside surface—Rose Pink, Plate 427/3 at outer margin, becoming overlaid and blotched with Amaranth Rose, Plate 530/1 towards base, with point of attachment Primrose Yellow, Plate 601/2; inside surface—Pastel Lilac, Plate 437, grading to a slightly darker shade of Pastel Mauve, Plate 433, with point of attachment Primrose Yellow, Plate 601.

*General color effect.*—Newly opened flower—slightly darker than Pastel Lilac, Plate 437. 3-days open—slightly darker than Pastel Lilac, Plate 437.

*Behavior.*—Drop off cleanly.

*Flower longevity.*—On bush in garden—4 days in June. Cut roses grown outdoors and kept at living-room temperatures—3 days in June.

*Reproductive organs*

Stamens: Many; arranged irregularly about pistils; mixed with petaloids.

Filaments: Medium length; most with anthers. Color—Sulphur Yellow, Plate 1/1.

Anthers: Medium size; all open at once; occasionally an anther fused with a petaloid. Color—Dresden Yellow, Plate 64/3.

Pollen: Moderate. Color—gold.

Pistils: Many.

Styles: Uneven; medium length; medium caliper; bunched.

Stigma: Color—white-yellow.

Ovaries: All enclosed in receptacle.

Hips: None observed.

Sepals: Permanent; moderately long; straight.

Seeds: None observed.

*Plant*

Foliage:

*Leaves.*—Compound of 5 leaflets; normal abundance; medium large; leathery; glossy.

*Leaflets.*—Shape—oval, with apex obtuse. Base—obtuse. Margin—simply serrate.

*Color.*—Mature: upper surface—Spinach Green, Plate 0960; under surface—Lavender Green, Plate 00076-. Young: upper surface—Spinach Green, Plate 0960/2, with a narrow margin of Garnet Brown, Plate 00918/3; under surface—Spinach Green, Plate 0960/3, overlaid with Erythrite Red, Plate 0027/1.

*Rachis (the supporting stem of the compound leaf).*—Medium. Upper side—grooved; hairy. Under side—sparsely prickly.

*Stipules.*—Moderately long; medium width; with short points turning out at an angle of 45°.

*Disease resistance.*—Comparable to that of the average variety, as determined by comparison with other varieties grown under the same cultural conditions at West Grove, Pennsylvania, U.S.A.

Growth:

*Habit.*—Bushy; much-branched.

*Growth.*—Free.

*Canes.*—Medium heavy.

*Main stems.*—Dull. Color—Parsley Green, Plate 00962. Prickles—several; color—Oxblood Red, Plate 00823/1. Hairs—none.

*Branches.*—Dull. Color—Parsley Green, Plate 00962. Prickles—several; color—Oxblood Red, Plate 00823/1. Hairs—none.

*New shoots.*—Color—Parsley Green, Plate 00962/2. Prickles—several; color—Purple Madder, Plate 1028. Hairs—none.

I claim:

A new and distinct variety of rose plant of the hybrid tea class, substantially as herein shown and described, characterized particularly as to novelty by the unique combination of a well-balanced and vigorous habit of growth, dark green foliage of medium size, excellently formed blooms which are considerably larger and have greater petalage than those of all other varieties in a similar color range, and a pure Pastel Lilac general color tonality of the blooms which is unusual in a rose of this class and which is retained without fading throughout the life of the bloom.

No references cited.